(12) United States Patent
Sakai et al.

(10) Patent No.: US 7,897,143 B2
(45) Date of Patent: *Mar. 1, 2011

(54) HAIR CLEANSING COMPOSITION

(75) Inventors: Hirokazu Sakai, Tokyo (JP); Hiroto Tanamachi, Tokyo (JP); Yoshimasa Okamoto, Tokyo (JP)

(73) Assignee: Kao Corporation, Tokyo (JP)

( * ) Notice: Subject to any disclaimer, the term of this patent is extended or adjusted under 35 U.S.C. 154(b) by 1167 days.

This patent is subject to a terminal disclaimer.

(21) Appl. No.: 10/743,836

(22) Filed: Dec. 24, 2003

(65) Prior Publication Data

US 2004/0156815 A1  Aug. 12, 2004

(30) Foreign Application Priority Data

Dec. 25, 2002  (JP) ................. 2002-375319

(51) Int. Cl.
*A61Q 5/02* (2006.01)

(52) U.S. Cl. ............... 424/70.19; 424/70.24; 424/70.31

(58) Field of Classification Search .......... None
See application file for complete search history.

(56) References Cited

U.S. PATENT DOCUMENTS

| | | | | |
|---|---|---|---|---|
| 4,835,148 A | * | 5/1989 | Barford et al. | 514/179 |
| 5,254,333 A | | 10/1993 | Kajino et al. | |
| 5,393,519 A | * | 2/1995 | Dowell et al. | 510/119 |
| 5,656,668 A | | 8/1997 | Motion et al. | |
| 5,661,118 A | | 8/1997 | Cauwet et al. | |
| 5,679,357 A | | 10/1997 | Dubief et al. | |
| 5,683,685 A | * | 11/1997 | Hirano et al. | 424/78.03 |
| 6,060,612 A | | 5/2000 | Hong et al. | |
| 6,121,482 A | | 9/2000 | Kwetkat et al. | |
| 6,379,659 B1 | | 4/2002 | Ishida et al. | |
| 6,555,100 B1 | | 4/2003 | Restle et al. | |
| 6,685,953 B1 | | 2/2004 | Hoshino et al. | |
| 7,544,648 B2 | * | 6/2009 | Sakai et al. | 510/126 |
| 2002/0010215 A1 | | 1/2002 | Shiroyama et al. | |
| 2003/0208858 A1 | * | 11/2003 | Hirano | 8/406 |
| 2003/0215410 A1 | * | 11/2003 | Hirano | 424/70.2 |
| 2003/0215416 A1 | * | 11/2003 | Hirano | 424/70.31 |
| 2005/0095217 A1 | * | 5/2005 | Hirano | 424/70.27 |

FOREIGN PATENT DOCUMENTS

| | | |
|---|---|---|
| EP | 0 739 625 | 10/1996 |
| EP | 1 166 766 | 1/2002 |
| JP | 4-134015 | 5/1992 |
| JP | 6-502660 | 3/1994 |
| JP | 8-59443 | 3/1996 |
| JP | 8-502058 | 3/1996 |
| JP | 10-226674 | 8/1998 |
| JP | 11-500715 | 1/1999 |
| JP | 11-222416 | 8/1999 |
| JP | 2000-510877 | 8/2000 |
| JP | 2001-316217 | 11/2001 |
| JP | 2003-500337 | 1/2003 |
| WO | WO00/61097 | 10/2000 |

OTHER PUBLICATIONS

U.S. Appl. No. 10/731,249, filed Dec. 10, 2003, Hoshino, et al.
U.S. Appl. No. 10/694,775, filed Oct. 29, 2003, Hirano.
U.S. Appl. No. 10/694,774, filed Oct. 29, 2003, Hirano.
U.S. Appl. No. 10/417,114, filed Apr. 17, 2003, Hirano.
U.S. Appl. No. 10/418,112, filed Apr. 18, 2003, Hirano.
U.S. Appl. No. 10/417,993, filed Apr. 18, 2003, Hirano.
U.S. Appl. No. 10/743,833, filed Dec. 24, 2003, Sakai, et a.
U.S. Appl. No. 10/743,834, filed Dec. 24, 2003, Sakai, et al.

* cited by examiner

*Primary Examiner* — Jyothsna A Venkat
(74) *Attorney, Agent, or Firm* — Oblon, Spivak, McClelland, Maier & Neustadt, L.L.P.

(57) ABSTRACT

Provided is a hair cleansing composition containing (A) an amphipathic amide lipid, (B) an anionic surfactant and (C) an organic or inorganic acid, or a salt thereof, and having a pH of from 1 to 4.5 when diluted with water to 20 times the weight. The hair cleansing composition of the present invention has advantages including protecting hair from physical or chemical stimulation and preventing split ends or breakage of hair without impairing the cleansing ability and feeling upon use, imparting hair with a pleasant feeling to the touch and moisture retention properties such as natural smoothness, moist feeling, and suppleness which healthy hair inherently possesses, and has excellent stability.

2 Claims, No Drawings

HAIR CLEANSING COMPOSITION

FIELD OF THE INVENTION

The present invention relates to acid hair cleansing compositions containing an amphipathic amide lipid.

BACKGROUND OF THE INVENTION

Since hair is daily exposed to physical stimulation by daily hair care routines such as heat drying with a hair dryer and brushing, and chemical stimulation by shampooing, permanent weaving, dyeing and bleaching, it is in a damaged state with a partial loss of components or structure. A change in hair quality due to ageing accelerates this damage and also causes the loss of suppleness which healthy hair inherently possesses.

It is a common practice to protect or repair hair in a damaged state by making up for the lost components or structure or an analogue thereof. Interaction (affinity) between a protecting base and hair is considered to be important for developing a protecting or restoring function, and thus a method of using a sphingolipid or protein derivative as a protecting base has been employed widely as a useful technique. For example, proposed is a hair cleansing composition containing a surfactant composed of an anionic surfactant and a bipolar ionic surfactant, a cationic polymer, and ceramide or glycoceramide (Japanese Patent Application Laid-Open No. 59443/1996). The composition however cannot contain a sufficient amount of a protecting base such as a ceramide or glycoceramide because it has a high melting point and is liable to crystallize. Moreover, even a slight amount of the protecting base incorporated in the composition does not readily penetrate into hair. No method has yet been proposed to feed hair with a sufficient amount of a protecting base. The conventional hair cleansing compositions are therefore accompanied by the problem that the protecting base incorporated therein cannot fully function.

SUMMARY OF THE INVENTION

According to the present invention, there is thus provided a hair cleansing composition containing the following components (A) to (C):

(A): an amphipathic amide lipid,
(B): an anionic surfactant, and
(C): an organic or inorganic acid, or a salt thereof,
and having a pH of from 1 to 4.5 at 25° C. when diluted with water to 20 times the weight.

DETAILED DESCRIPTION OF THE INVENTION

The present invention relates to a hair cleansing composition which allows a protecting base to sufficiently penetrate into hair and has excellent effects for preventing or repairing damaged hair.

The present inventors have found that acidification of the composition facilitates penetration of the amphipathic amide lipid serving as a protecting base into hair even in a cleansing composition system, thereby making it possible to protect hair from physical or chemical stimulation, suppress generation of split ends or breakage of hair, and at the same time impart hair with a pleasant feeling to the touch such as natural smoothness, moist feeling, and suppleness which healthy hair inherently possesses.

The amphipathic amide lipid as Component (A) preferably has 1 or 2 amide groups; preferably has, as a carbon chain bonded to the carbonyl group of the amide group, a $C_{5-60}$ alkyl or alkylene group which may be substituted with a hydroxy group and may contain an ester bond in its main chain; and preferably contains 1 to 5 hydroxy or $C_{1-30}$ alkoxy groups in total. The following compounds (1) to (4) are specific preferred examples of the amphipathic amide lipid.

(1) Diamide compounds represented by formula (1):

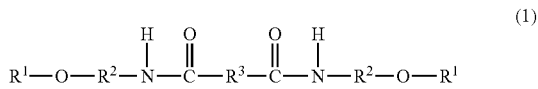

wherein, $R^1$ represents a linear or branched $C_{1-12}$ hydrocarbon group which may be substituted with a hydroxy group(s) and/or alkoxy group(s), $R^2$ represents a linear or branched divalent $C_{1-5}$ hydrocarbon group and $R^3$ represents a linear or branched divalent $C_{1-22}$ hydrocarbon group.

As $R^1$ in formula (1), linear or branched $C_{1-12}$ alkyl groups which may be substituted with 1 to 3 groups selected from the group consisting of a hydroxy group and $C_{1-6}$ alkoxy groups are preferred. Of these, unsubstituted $C_{1-12}$ alkyl groups and $C_{2-12}$ alkyl groups substituted with 1 to 2 hydroxy groups and one $C_{1-6}$ alkoxy group or with one hydroxy group and one $C_{1-6}$ alkoxy group are more preferred. Specific examples include methyl, ethyl, propyl, butyl, hexyl, dodecyl, 2-methylpropyl, 2-ethylhexyl, 2-hydroxyethyl, 9-hydroxynonyl, 2,3-dihydroxypropyl, 2-methoxyethyl, 2-hydroxy-3-methoxypropyl and 9-methoxynonyl groups, of which 2-hydroxyethyl, methyl, dodecyl and 2-methoxyethyl groups are preferred.

As $R^2$ in formula (1), linear or branched $C_{2-5}$ alkylene groups are preferred, and linear or branched $C_{2-3}$ alkylene groups are preferred. Specific examples include ethylene, trimethylene, tetramethylene, pentamethylene, 1-methylethylene, 2-methylethylene, 1-methyltrimethylene, 2-methyltrimethylene, 1,1-dimethylethylene and 2-ethyltrimethylene groups. Of these, ethylene and trimethylene groups are preferred.

As $R^3$ in formula (1), linear or branched divalent $C_{2-22}$ hydrocarbon groups are preferred, and linear or branched $C_{11-22}$ alkylene groups and alkenylene groups having 1 to 4 double bonds are more preferred. Specific examples include ethylene, trimethylene, tetramethylene, hexamethylene, heptamethylene, octamethylene, decamethylene, undecamethylene, dodecamethylene, tridecamethylene, tetradecamethylene, hexadecamethylene, octadecamethylene, 1-methylethylene, 2-ethyltrimethylene, 1-methylheptamethylene, 2-methylheptamethylene, 1-butylhexamethylene, 2-methyl-5-ethylheptamethylene, 2,3,6-trimethylheptamethylene, 6-ethyldecamethylene, 7-methyltetradecamethylene, 7-ethylhexadecamethylene, 7,12-dimethyloctadecamethylene, 8,11-dimethyloctadecamethylene, 7,10-dimethyl-7-ethylhexadecamethylene, 1-octadecylethylene, ethenylene, 1-octadecenylethylene, 7,11-octadecadienylene, 7-ethenyl-9-hexadecamethylene, 7,12-dimethyl-7,11-octadecadienylene and 8,11-dimethyl-7,11-octadecadienylene groups. Of these, 7,12-dimethyloctadecamethylene, 7,12-dimethyl-7,11-octadecadienylene, octadecamethylene, undecamethylene and tridecamethylene groups are preferred.

Preferred diamide compounds (1) are compounds having the above-described preferred groups as $R^1$, $R^2$ and $R^3$, respectively. Specific examples are the following compounds:

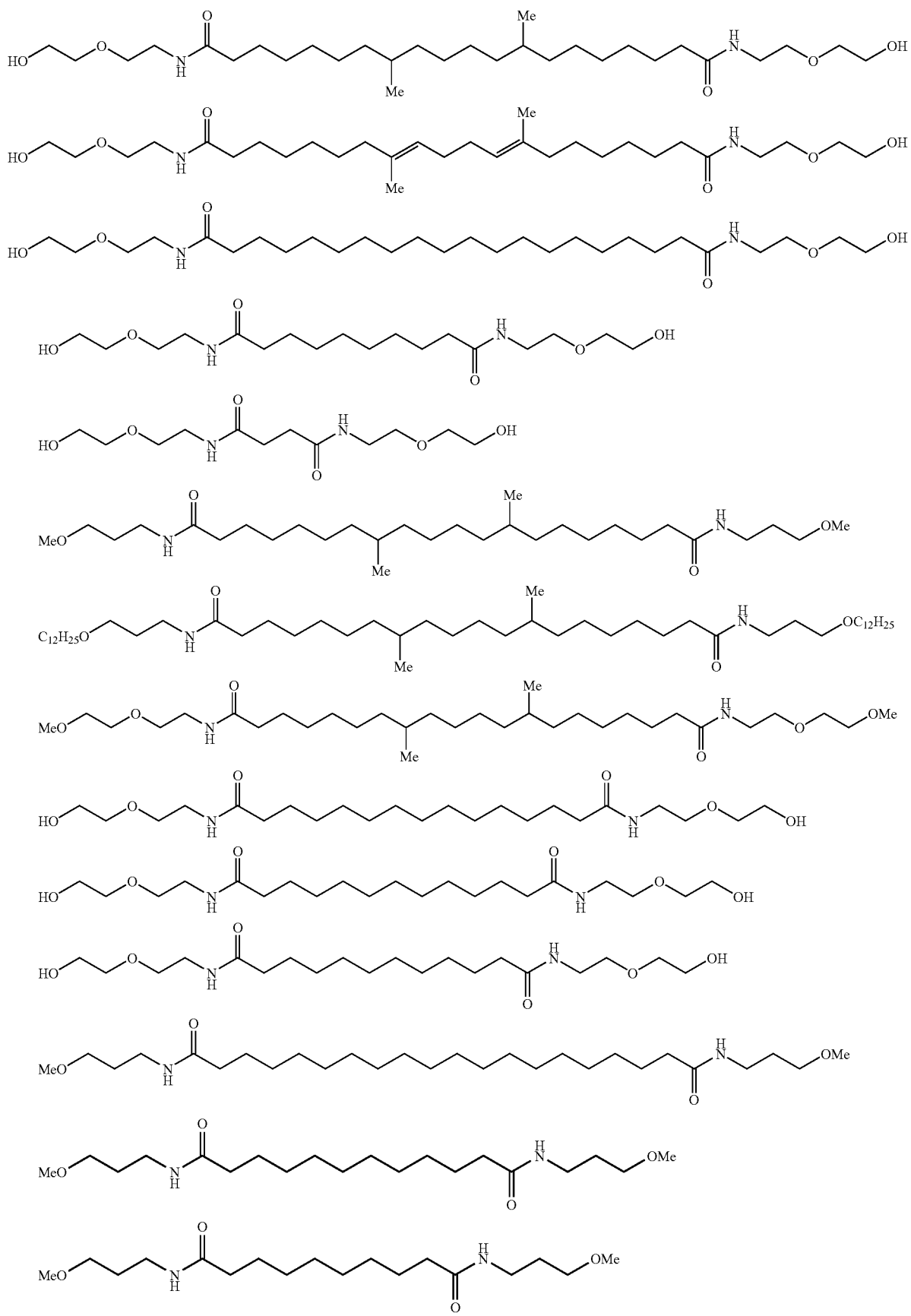

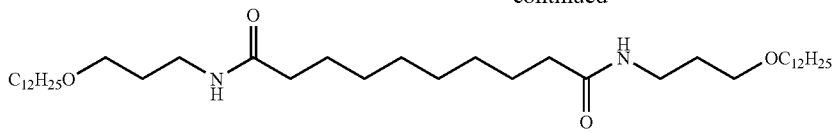

(2) Ceramides represented by the following formula (2):

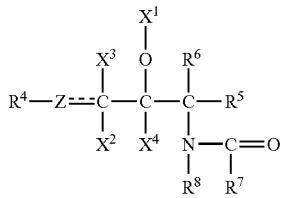

wherein, $R^4$ represents a linear, branched or cyclic, saturated or unsaturated $C_{4-30}$ hydrocarbon group which may be substituted with hydroxy, oxo or amino group(s), Z represents a methylene group, a methine group or an oxygen atom, a broken line represents the presence or absence of a π bond, $X^1$ represents a hydrogen atom, an acetyl group or a glyceryl group, or, together with the adjacent oxygen atom, forms an oxo group, $X^2$, $X^3$ and $X^4$ each independently represents a hydrogen atom, a hydroxy group or an acetoxy group (with the proviso that when Z represents a methine group, one of $X^2$ and $X^3$ represents a hydrogen atom and the other does not exist, and when —O—$X^1$ represents an oxo group, $X^4$ does not exist), $R^5$ and $R^6$ each independently represents a hydrogen atom, a hydroxy group, a hydroxymethyl group or an acetoxymethyl group, $R^7$ represents a linear, branched or cyclic, saturated $C_{5-35}$ hydrocarbon group which may be substituted with a hydroxy or amino group, or the saturated $C_{5-35}$ hydrocarbon group in which a linear, branched or cyclic, saturated or unsaturated $C_{8-22}$ fatty acid which may be substituted with hydroxy group(s) is ester-bonded at the ω-position of the hydrocarbon group, and $R^8$ represents a hydrogen atom or a linear or branched, saturated or unsaturated hydrocarbon group which may have substituent(s) selected from a hydroxy group, hydroxyalkoxy groups, alkoxy groups and an acetoxy group, and has 1 to 8 carbon atoms in total.

As $R^4$ in formula (2), linear, branched or cyclic, saturated or unsaturated $C_{7-22}$ hydrocarbon groups which may be substituted with hydroxy group(s) are preferred. As $X^1$, a hydrogen atom and a glyceryl group are preferred. It is preferred that none or one of $X^2$, $X^3$, and $X^4$ represents a hydroxy group and the others represent a hydrogen atom. It is preferred that one of $R^5$ and $R^6$ represents a hydrogen atom or a hydroxymethyl group and the other represents a hydrogen atom. In $R^7$, preferred examples of the fatty acid which may be ester-bonded or amide-bonded to the saturated hydrocarbon group at the ω-position thereof include isostearic acid, 12-hydroxystearic acid and linoleic acid. As $R^8$, a hydrogen atom and hydrocarbon groups which may be substituted with 1 to 3 substituents selected from a hydroxy group, hydroxyalkoxy groups and alkoxy groups and have 1 to 8 carbon atoms in total are preferred.

As ceramide (2), preferred are the following compounds (2a) and (2b).

(2a) Natural ceramides or natural type ceramides represented by formula (2a), and derivatives thereof (which will hereinafter be called "natural type ceramides")

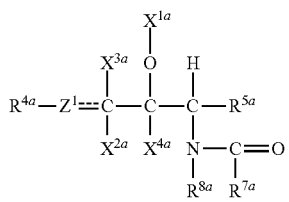

wherein, $R^{4a}$ represents a linear, branched or cyclic, saturated or unsaturated $C_{7-19}$ hydrocarbon group which may be substituted with a hydroxy group, $Z^1$ represents a methylene or methine group, a broken line represents the presence or absence of a π bond, $X^{1a}$ represents a hydrogen atom or, together with the adjacent oxygen atom, forms an oxo group, $X^{2a}$, $X^{3a}$ and $X^{4a}$ each independently represents a hydrogen atom, a hydroxy group or an acetoxy group (with the proviso that when $Z^1$ represents a methine group, one of $X^{2a}$ and $X^{3a}$ represents a hydrogen atom and the other does not exist, and when —O—$X^{1a}$ represents an oxo group, $X^{4a}$ does not exist), $R^{5a}$ represents a hydroxymethyl group or an acetoxymethyl group, $R^{7a}$ represents a linear, branched or cyclic, saturated $C_{5-30}$ hydrocarbon group which may be substituted with hydroxy group(s), or the saturated $C_{5-30}$ hydrocarbon group in which a linear or branched, saturated or unsaturated $C_{8-22}$ fatty acid which may be substituted with hydroxy group(s) is ester-bonded at the ω-position of the hydrocarbon group, and $R^{8a}$ represents a hydrogen atom or a $C_{1-4}$ alkyl group.

Preferred are compounds in which $R^{4a}$ is a linear $C_{7-19}$, more preferably $C_{13-15}$ alkyl group, $Z^1$ is a methine group, one of $X^{2a}$ and $X^{3a}$ is a hydrogen atom, and $R^{7a}$ is a linear $C_{9-27}$ alkyl group which may be substituted with hydroxy group(s). In addition, $X^{1a}$ preferably represents a hydrogen atom or, together with an oxygen atom, forms an oxo group. More preferred examples of $R^{7a}$ include a tricosyl group, a 1-hydroxypentadecyl group, a 1-hydroxytricosyl group, a heptadecyl group, a 1-hydroxyundecyl group and a nonacosyl group having a linoleic acid ester-bonded at the ω-position of the group.

Specific examples of the natural type ceramides include Ceramide Types 1 to 7 having the below-described structures and obtained by amidation of sphingosine, dihydrosphingosine, phytosphingosine or sphingadienine (for example, FIG. 2 of J. Lipid Res., 24, 759(1983), and pig and human ceramides as described in FIG. 4 of J. Lipid Res., 35, 2069 (1994)).

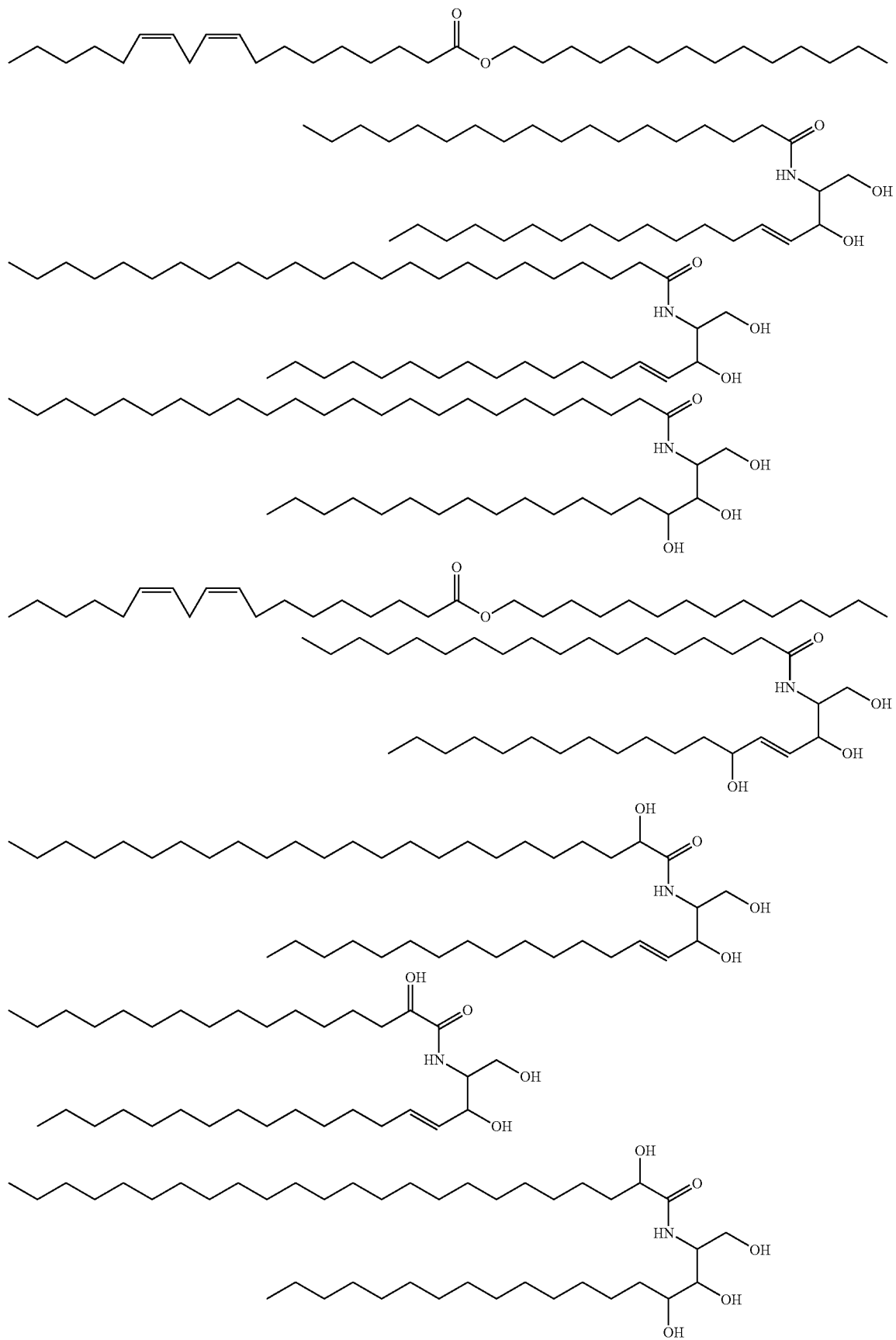

-continued

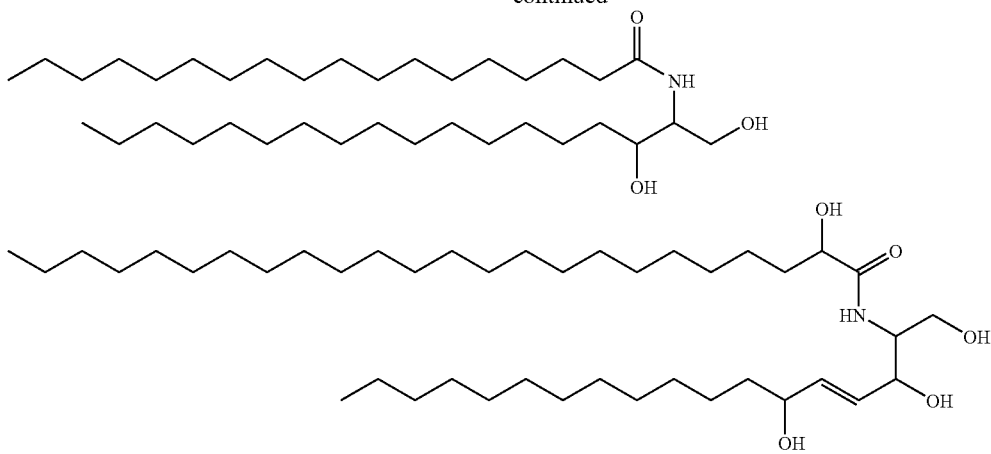

Examples also include N-alkyl derivatives (for example, N-methyl derivatives) of the above-described ceramides. They may be either a natural extract or synthesized product. Commercially available ones are also usable.

(2b) Pseudo type ceramides represented by the following formula (2b):

$$\begin{array}{c} X^{1b} \\ | \\ H \quad O \quad H \\ | \quad | \quad | \\ R^{4b}-O-C-C-C-H \\ | \quad | \quad | \\ H \quad H \quad N-C=O \\ | \quad | \\ R^{8b} \quad R^{7b} \end{array} \quad (2a)$$

wherein, $R^{4b}$ represents a linear, branched or cyclic, saturated or unsaturated $C_{10-22}$ hydrocarbon group which may be substituted with hydroxy group(s), $X^{1b}$ represents a hydrogen atom, an acetyl group or a glyceryl group, $R^{7b}$ represents a linear, branched or cyclic, saturated or unsaturated $C_{5-22}$ hydrocarbon group which may be substituted with hydroxy or amino group(s), or the hydrocarbon group in which a linear or branched, saturated or unsaturated $C_{8-22}$ fatty acid which may be substituted with hydroxy group(s) is ester-bonded at the ω-position of the hydrocarbon group, and $R^{8b}$ represents a hydrogen atom or an alkyl group which may be substituted with hydroxy group(s), hydroxyalkoxy group(s), alkoxy group(s) or acetoxy group(s) and has 1 to 8 carbon atoms in total.

Preferred as $R^{7b}$ are a nonyl group, a tridecyl group, a pentadecyl group, an undecyl group having linoleic acid ester-bonded at the ω-position of the group, a pentadecyl group having linoleic acid ester-bonded at the ω-position of the group, a pentadecyl group having 12-hydroxystearic acid ester-bonded at the ω-position of the group, and an undecyl group having methyl-branched isostearic acid amide-bonded at the ω-position of the group. As the hydroxyalkoxy or alkoxy groups for $R^{8b}$, preferred are those having 1 to 8 carbon atoms.

As the pseudo type ceramides (2b), those having as $R^{4b}$ a hexadecyl group, as $X^{1b}$ a hydrogen atom, as $R^{7b}$ a pentadecyl group, and as $R^{8b}$ a hydroxyethyl group; those having as $R^{4b}$ a hexadecyl group, as $X^{1b}$ a hydrogen atom, as $R^{7b}$ a nonyl group, and as $R^{8b}$ a hydroxyethyl group; or those having as $R^{4b}$ a hexadecyl group, as $X^{1b}$ a glyceryl group, as $R^{7b}$ a tridecyl group, and as $R^{8b}$ a 3-methoxypropyl group are preferred, with those having as $R^{4b}$ a hexadecyl group, as $X^{1b}$ a hydrogen atom, as $R^{7b}$ a pentadecyl group, and as $R^{8b}$ a hydroxyethyl group being more preferred. Specific preferred examples include those represented by the following formulas:

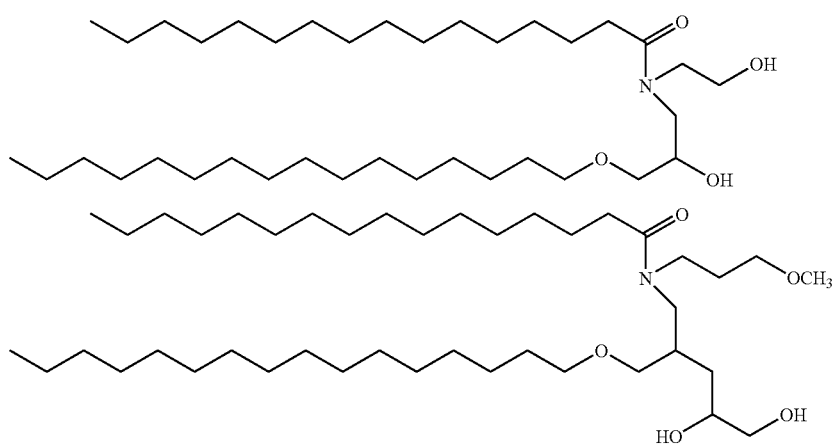

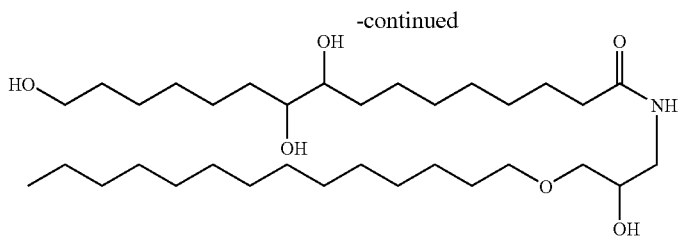

(3) Diamide compounds represented by the following formula (3):

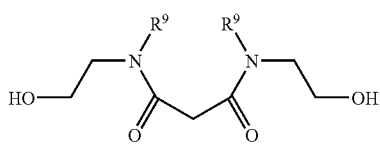

wherein, $R^9$ represents a $C_{10-18}$ alkyl group which may be substituted with hydroxy group(s).

Specific examples of compound (3) include the compound represented by the following formula:

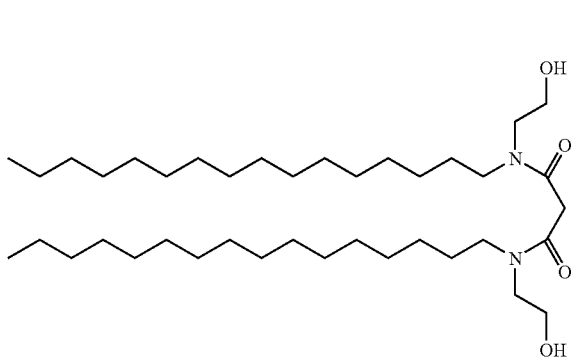

(4) Amide compounds represented by the following formula (4):

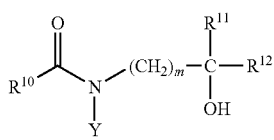

wherein, $R^{10}$ represents a linear or branched, saturated or unsaturated $C_{9-31}$ alkyl group which may be substituted with hydroxy group(s), or a 2-dodecen-1-yl succinic acid residue, m stands for an integer of from 1 to 3, $R^{11}$ and $R^{12}$ each represents a hydrogen atom or a $C_{1-4}$ alkyl or hydroxyalkyl group, Y represents a linear or branched, saturated or unsaturated $C_{10-32}$ alkyl group which may be substituted with hydroxy group(s), or a substituent represented by the following formula:

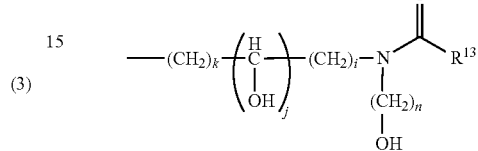

in which, k, i and n each stands for an integer of from 1 to 3, j stands for 0 or 1, and $R^{13}$ represents a linear or branched, saturated or unsaturated $C_{9-31}$ alkyl group which may be substituted with hydroxy group(s).

Specific examples of Compound (4) include a compound represented by the following formula:

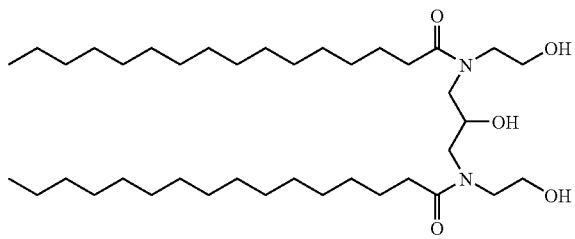

Of the above-described amphipathic amide lipids, those represented by formula (1) or (2) are preferred, and those represented by formula (1) are more preferred.

As Component (A), two or more of these amphipathic amide lipids may be used in combination. Its (their) content in the hair cleansing composition of the present invention is preferably by weight of the composition, from 0.001 to 20 wt. %, more preferably from 0.1 to 15 wt. %, even more preferably from 0.2 to 3 wt. % in view of imparting suppleness to hair and preventing split ends or breakage of hair.

The anionic surfactants as Component (B) include alkyl (or alkenyl) sulfates, polyoxyalkylene alkyl (or alkenyl) ether sulfates, alkane sulfonates, olefin sulfonates, alkylbenzene sulfonates, alkyl (or alkenyl) sulfosuccinates, dialkyl (or dialkenyl) sulfosuccinates, polyoxyalkylene alkyl (or alkenyl) sulfosuccinates, alkyl (or alkenyl) ether carboxylates, polyoxyalkylene alkyl (or alkenyl) ether carboxylates, polyoxyalkylene alkyl (or alkenyl) ether phosphates, fatty acid salts, N-acyl glutamates, N-acyl taurates, and N-acylmethyltaurine. Of these, polyoxyethylene alkyl ether sulfates, polyoxyethylene alkenyl ether sulfates and alkyl sulfates are preferred, with those represented by the below-described formula (B1) or (B2) being more preferred.

$$R^{14}O(CH_2CH_2O)_aSO_3M \qquad (B1)$$

$$R^{15}OSO_3M \qquad (B2)$$

wherein, $R^{14}$ represents a $C_{10-18}$ alkyl or alkenyl group, $R^{15}$ represents a $C_{10-18}$ alkyl group, M represents an alkali metal, alkaline earth metal, ammonium, alkanolamine or basic amino acid, and a is a weight average number of from 1 to 5.

As Component (B), two or more of the above-described compounds may be used in combination. Its (their) content in the hair cleansing composition of the present invention is preferably by weight of the composition, from 1 to 50 wt. %, more preferably from 8 to 30 wt. %, even more preferably from 10 to 22 wt. % from the viewpoint of foaming properties, liquid properties during use and cleansing ability.

Examples of the organic acid as Component (C) include carboxylic acids such as monocarboxylic acids, dicarboxylic acids, hydroxycarboxylic acids and polycarboxylic acids, alkylsulfuric acids and alkylphosphoric acids. Of these, carboxylic acids are preferred and dicarboxylic acids and hydroxycarboxylic acids are more preferred. The dicarboxylic acids include malonic acid, succinic acid, glutaric acid, adipic acid, maleic acid, fumaric acid, phthalic acid and glutamic acid, of which glutamic acid is preferred. The hydroxycarboxylic acids include glycolic acid, lactic acid, hydroxyacrylic acid, oxybutyric acid, glyceric acid, malic acid, tartaric acid and citric acid, of which α-hydroxycarboxylic acids are preferred and lactic acid, malic acid and glycolic acid are more preferred. Examples of the inorganic acid include phosphoric acid, sulfuric acid and nitric acid, with phosphoric acid being preferred.

As Component (C), two or more of the above-described organic or inorganic acids, or salts thereof may be used in combination. Its (their) content in the hair cleansing composition of the present invention is, in terms of an acid, preferably by weight of the composition, from 0.05 to 10 wt. %, more preferably from 0.1 to 5 wt. % even more preferably from 0.5 to 2 wt. % in view of promoting the penetration of Component (A) (amphipathic amide lipid) into hair.

For improving foaming performance, a surfactant other than Component (B), preferably a nonionic surfactant or amphoteric surfactant may be incorporated in the hair cleansing composition of the present invention.

Examples of the nonionic surfactant include polyoxyalkylene sorbitan fatty acid esters, polyoxyalkylene sorbitol fatty acid esters, polyoxyalkylene glycerin fatty acid esters, polyoxyalkylene fatty acid esters, polyoxyalkylene alkyl ethers, polyoxyalkylene alkylphenyl ethers, polyoxyalkylene (hydrogenated) castor oils, sucrose fatty acid esters, polyglycerin alkyl ethers, polyglycerin fatty acid esters, fatty acid alkanolamides, alkyl glycosides and glyceryl ethers. Of these, alkyl glycosides, polyoxyalkylene ($C_8$ to $C_{20}$) fatty acid esters, polyoxyethylene sorbitan fatty acid esters, polyoxyethylene hydrogenated castor oils and fatty acid alkanolamides are preferred. As the fatty acid alkanolamides, those having a $C_{8-18}$ acyl group are preferred and those having a $C_{10-16}$ acyl group are more preferred. As the fatty acid alkanolamides, either monoalkanolamides or dialkanolamides may be used, with those having a $C_{2-3}$ hydroxyalkyl group being preferred. Examples thereof include oleic diethanolamide, palm kernel fatty acid diethanolamide, coconut oil fatty acid diethanolamide, lauric acid diethanolamide, polyoxyethylene coconut oil fatty acid monoethanolamide, coconut oil fatty acid monoethanolamide, lauric acid isopropanolamide and lauric acid monoethanolamide.

As the amphoteric surfactant, betaine surfactants are included. Of these, betaine surfactants such as alkyldimethylaminoacetic acid betaines and fatty acid amidopropyl betaines are preferred, with fatty acid amidopropyl betaines being more preferred. As the fatty acid amidopropyl betaines, those having a $C_{8-18}$ acyl group are preferred and those having $C_{10-16}$ acyl group are more preferred, with laurylamidopropyl betaine, palm kernelamidopropyl betaine and cocamidopropyl betaine being even more preferred.

Two or more of these surfactants may be used in combination. Its (or their) content in the whole composition is preferably from 0.01 to 20 wt. %, more preferably from 0.05 to 10 wt. %, even more preferably from 0.1 to 5 wt. %.

To the hair cleansing composition of the present invention, silicone derivatives or cationic polymers ordinarily employed for giving a pleasant feel can be added further for improving the feeling upon use.

Examples of the silicone derivatives include dimethylpolysiloxane, methylphenylpolysiloxane, amino-modified silicones, polyether-modified silicones, epoxy-modified silicones, fluorine-modified silicones, cyclic silicones, alkyl-moldified silicones and oxazoline-modified silicones, of which dimethylpolysiloxane, methylphenylpolysiloxane, amino-modified silicones, polyether-modified silicones, oxazoline-modified silicones and cyclic silicones are preferred. Two or more of these silicones may be used in combination. Its (or their) content in the whole composition is preferably from 0.01 to 20 wt. %, more preferably from 0.05 to 10 wt. %, even more preferably from 0.1 to 5 wt. %.

Examples of the cationic polymer include polydimethyldiallylammonium chlorides, acrylamidopropyltrimethylammonium chloride/acrylate copolymers, acrylamide/dimethyldiallylammonium chloride copolymers, methylvinylimidazolinium chloride/vinylpyrrolidone copolymers, hydroxyethyl cellulose/diallyldimethylammonium chloride copolymers, diethylsulfates of vinylpyrrolidone/dimethylaminoethyl methacrylate copolymers, vinylpyrrolidone/dimethylaminoethyl methacrylate copolymers, vinylpyrrolidone/alkylaminoacrylate/vinylcaprolactam copolymers, vinylpyrrolidone/dimethylaminopropylmethacrylamide copolymers, chlorinated O-[2-hydroxy-3-(trimethylammonio)propyl]hydroxy cellulose, and guar hydroxypropyltrimonium chloride. Of these, chlorinated 0-[2-hydroxy-3-(trimethylammonio)propyl]hydroxy cellulose and guar hydroxypropyltrimonium chloride are preferred from the viewpoint of the feeling. Two or more of these cationic polymers may be used in combination. Its (or their) content in the whole composition is, as a solid content, preferably from 0.01 to 20 wt. %, more preferably from 0.05 to 10 wt. %, even more preferably from 0.1 to 5 wt. %.

The hair cleansing composition of the present invention can contain, in addition to the above-described components, oil components such as higher alcohols, lanolin derivatives, and polyethylene glycol fatty acid esters; water soluble polymers such as hydroxypropylmethyl cellulose, hydroxy cellulose, polyvinyl alcohol, and polyethylene glycol; polyhydric alcohols such as sorbitol; humectants; chelating agents such as ethylenediaminetetraacetic acid (EDTA); drugs such as vitamin preparations; amino acids and derivatives thereof; fine particles of a polymer such as polyethylene, polystyrene, poly(methyl methacrylate), nylon or silicone, and hydrophobic products thereof; extracts derived from animals or plants; ultraviolet absorbers; pearling agents; antiseptics; bactericides; pH regulators; colorants; and fragrances, according to the intended use.

The hair cleansing composition of the present invention is adjusted to have a pH of from 1 to 4.5 upon application to hair (diluted with water to 20 times the weight of the composition; at 25° C.). This allows for example, Component (A) (amphipathic amide lipid) to sufficiently penetrate into hair and prevents irritation. The pH of the composition is preferably from 2 to 4, more preferably from 3 to 4.

The hair cleansing composition of the present invention can be provided in any form such as liquid, powder, gel or granule as needed. A liquid composition using water or a lower alcohol as a solvent is preferred, with an aqueous solution being more preferred.

EXAMPLES

The following examples further describe and demonstrate embodiments of the present invention. The examples are given solely for the purpose of illustration and are not to be construed as limitations of the present invention. In the below-described Examples and Comparative Examples, the following amphipathic amide lipids were employed.

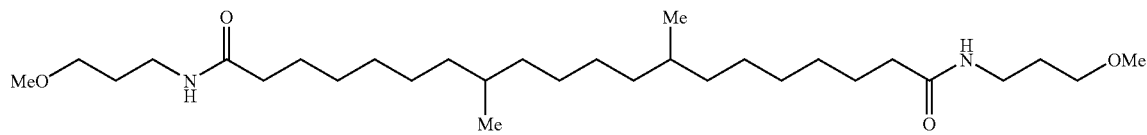

Amphipathic amide lipid A

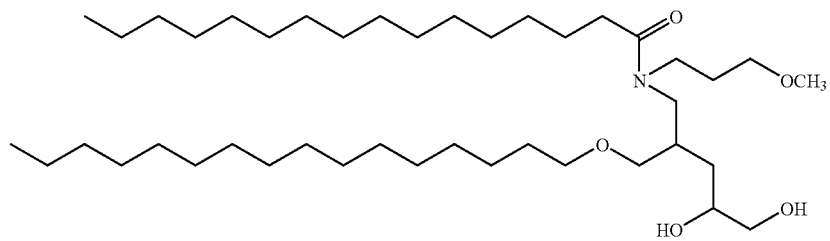

Amphipathic amide lipid B

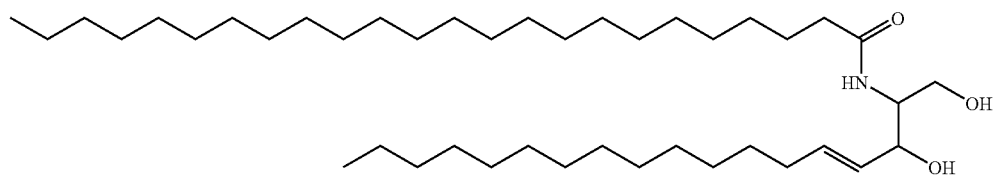

Amphipathic amide lipid C  Ceramide 2

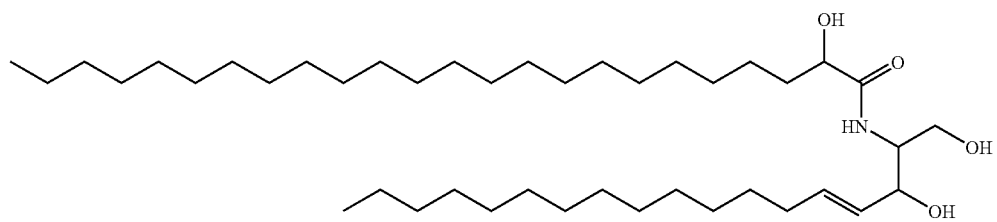

Amphipathic amide lipid D  Ceramide 5

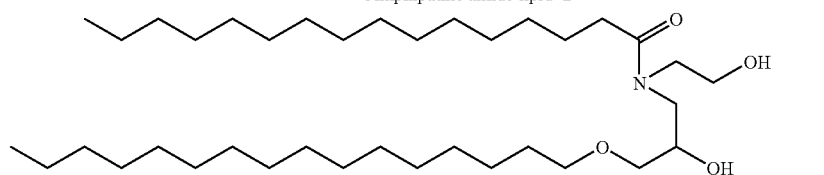

Amphipathic amide lipid E

The pH in the description below is a value of the composition diluted with water to 20 times the weight of the composition when measured at 25° C.

Examples 1 to 3

And Comparative Examples 1 to 3

Shampoos as shown in Table 1 were prepared in a conventional manner and they were evaluated.

(1) Smoothness and Moist Feeling

A bundle of 20 g (15 cm in length) of the hair of a healthy Japanese female was made and 1 g of the shampoo in Table 1 was applied to the hair bundle. After one minute of foaming upon application, the hair was rinsed with running water for 30 seconds, followed by towel drying and then drying with a hair dryer. The "smoothness" and "moist feeling" of the dried hair were organoleptically evaluated in accordance with the following criteria: Smoothness:

A: The hair is imparted with natural and sufficient smoothness.

B: The hair is imparted with smoothness.

C: It is difficult to evaluate whether the hair is imparted with smoothness or not.

D: Friction appears among individual hairs.

Moist Feeling:

A: The hair became very moist to the touch.

B: The hair became moist to the touch.

C: It is difficult to evaluate whether the hair became moist to the touch or not.

D: The hair does not become moist to the touch.

(2) The Physical Property-Recovering Ratio of Hair

About 20 g (about 15 to 20 cm in length) of the hair of a Japanese female, which had not been subjected to any chemical treatment such as permanent waving and hair dyeing, was treated eight times with "LAVENUS High Bleach" (trade name; product of Kao Corporation) (bath ratio 1:1), each at 40° C. for 20 minutes. After each bleaching treatment, cleansing with a plain shampoo and a plain rinse was conducted 90 times, 720 times in total. The plain shampoo and plain rinse used here have the following compositions, respectively:

| | (wt. %) |
|---|---|
| Plain Shampoo | |
| A 25 wt. % solution of sodium polyoxyethylene (2.5) lauryl ether sulfate | 62.0 |
| Lauric acid diethanolamide | 2.28 |
| Disodium edetate | 0.10 |
| Sodium benzoate | 0.50 |
| Oxybenzone | 0.03 |
| Phosphoric acid (75 wt. %) | 0.10 |
| Dibutylhydroxytoluene | 0.01 |
| Sodium chloride | 0.80 |
| Red No. 106 | 0.00012 |
| Fragrance | 0.26 |
| Purified water | Balance |
| Plain Rinse | |
| Stearyltrimethylammonium chloride (28 wt. %) | 2.7 |
| Distearyldimethylammonium chloride | 3.6 |
| Cetanol | 2.0 |
| Propylene glycol | 5.0 |
| Methyl p-hydroxybenzoate | 0.1 |
| Deionized water | Balance |

Dynamic viscoelasticity (storage elastic modulus E': corresponding to the hardness of hair, unit: [Pa]) of each of a hair bundle (healthy hair) without treatment, a hair bundle subjected to the above-described bleaching treatment and a hair bundle shampooed with the shampoo of Table 1 30 times after the bleaching treatment was measured using a dynamic viscoelasticity-measuring apparatus "DMTA V" (trade name; product of Rheometric Scientific FE).

Measuring Conditions

Temperature: 22±1° C., relative humidity: 20±1% RH, frequency: 10 Hz

Criteria for Evaluation

A physical property-recovering ratio of hair R represented by the following equation:

$$R=(E_1'-E_n')/(E_1'-E_0')\times 100$$

wherein, $E_0'$ represents a storage elastic modulus of the healthy hair, $E_1'$ represents a storage elastic modulus of the bleached hair and $E_n'$ represents a storage elastic modulus of the hair shampooed 30 times with each sample after bleaching, was calculated as an index of how the physical properties of hair damaged by the bleaching treatment were recovered by the treatment with each sample of Table 1 compared with those of hair before bleaching (untreated hair), and each sample was evaluated based on the below-described criteria:

A: not less than 70 and up to 100

B: not less than 50 but less than 70

C: less than 50

TABLE 1

| | | | Examples | | | Comparative Examples | | (wt. %) |
|---|---|---|---|---|---|---|---|---|
| | | | 1 | 2 | 3 | 1 | 2 | 3 |
| (A) | Amphipathic amide lipid A | | 2 | 2 | — | 2 | — | — |
| | Amphipathic amide lipid B | | — | — | 2 | — | — | — |
| (B) | Sodium polyoxyethylene (2) lauryl ether sulfate | | 10 | 10 | 10 | 10 | 10 | 10 |
| | Sodium lauryl sulfate | | 5 | 5 | 5 | 5 | 5 | 5 |
| (C) | Lactic acid | | 1 | — | 1 | 1 | 1 | — |
| | Malic acid | | — | 1 | — | — | — | — |
| Others | Myristyl alcohol | | 1 | 1 | 1 | 1 | 1 | 1 |
| | Cocoylmonoethanolamide | | 0.5 | 0.5 | 0.5 | 0.5 | 0.5 | 0.5 |
| | Ethylene glycol distearate | | 1 | 1 | 1 | 1 | 1 | 1 |

TABLE 1-continued

|  |  | Examples | | | Comparative Examples | | (wt. %) |
| --- | --- | --- | --- | --- | --- | --- | --- |
|  |  | 1 | 2 | 3 | 1 | 2 | 3 |
|  | Cationized hydroxyethyl cellulose | 0.3 | 0.3 | 0.3 | 0.3 | 0.3 | 0.3 |
|  | Cationized guar gum | 0.5 | 0.5 | 0.5 | 0.5 | 0.5 | 0.5 |
|  | PH regulator (sodium hydroxide, citric acid) | q.s.* | q.s.* | q.s.* | q.s.* | q.s.* | q.s.* |
|  | Purified water | Balance | Balance | Balance | Balance | Balance | Balance |
|  | pH | 3.5 | 3.5 | 3.5 | 5 | 3.5 | 6 |
| Evaluation | Smoothness of hair | A | A | A | C | C | C |
|  | Moist feeling of hair | A | A | A | C | C | C |
|  | Physical property-recovering ratio of hair | A | A | B | C | C | C |

*An amount to adjust the pH

Example 4

Clear Shampoo

|  | (wt. %) |
| --- | --- |
| Sodium polyoxyethylene (2) lauryl ether sulfate | 10.0 |
| Sodium lauryl sulfate | 5.0 |
| Cationized guar gum | 0.1 |
| Amphipathic amide lipid A | 0.2 |
| Malic acid | 0.75 |
| Sodium chloride | 1.0 |
| Laurylamidopropyl betaine | 1.0 |
| Cocoylmonoethanolamide | 0.3 |
| Propylene carbonate | 0.5 |
| Glycerin | 1.0 |
| Sodium hydroxide | An amount to adjust the pH |
| Deionized water | balance |

The above-described shampoo (pH 4.0) can provide hair with good smoothness, moist feeling and suppleness after use.

Example 5

Conditioning Shampoo

|  | (wt. %) |
| --- | --- |
| Sodium polyoxyethylene (2) lauryl ether sulfate | 8.0 |
| Sodium lauryl sulfate | 5.0 |
| Cationized guar gum | 0.5 |
| Amphipathic amide lipid A | 2.0 |
| Maleic acid | 0.75 |
| Trisodium citrate | 1.0 |
| Laurylamidopropyl betaine | 3.0 |
| 2-Ethylhexyl monoglyceryl ether | 0.7 |
| Myristyl alcohol | 1.0 |
| Ethylene glycol distearate | 3.0 |
| Polypropylene glycol (Mw = 400) | 0.5 |
| Glycerin | 1.0 |
| Sodium hydroxide | An amount to adjust the pH |
| Deionized water | balance |

The above-described shampoo (pH 3.5) can provide hair with good smoothness, moist feeling and suppleness after use.

Example 6

Conditioning Shampoo

|  | (wt. %) |
| --- | --- |
| Sodium polyoxyethylene (2) lauryl ether sulfate | 11.0 |
| Sodium lauryl sulfate | 5.0 |
| Cationized guar gum | 0.3 |
| Amphipathic amide lipid B | 2.0 |
| Malic acid | 0.75 |
| Lactic acid | 0.1 |
| Sodium chloride | 0.2 |
| Benzyl alcohol | 0.5 |
| Cocoylmonoethanolamide | 1.0 |
| Myristyl alcohol | 1.0 |
| Cetanol | 0.5 |
| Ethylene glycol distearate | 3.0 |
| Cationic hydroxyethyl cellulose | 0.3 |
| Glycerin | 1.0 |
| Sodium hydroxide | An amount to adjust the pH |
| Deionized water | balance |

The above-described shampoo (pH 3.7) can provide hair with good smoothness, moist feeling and suppleness after use.

Example 7

Conditioning Shampoo

|  | (wt. %) |
| --- | --- |
| Sodium polyoxyethylene (2) lauryl ether sulfate | 8.0 |
| Cationized guar gum | 0.3 |
| Amphipathic amide lipid C | 0.05 |
| Amphipathic amide lipid D | 0.1 |
| Malic acid | 0.5 |
| Lactic acid | 0.5 |
| Sodium chloride | 1.0 |
| Laurylamidopropyl betaine | 3.0 |
| Myristyl alcohol | 1.0 |
| Cetanol | 0.5 |
| Behentrimonium chloride | 0.5 |
| Ethylene glycol distearate | 2.0 |
| Benzyloxyethanol | 0.5 |

-continued

| | (wt. %) |
|---|---|
| Sodium hydroxide | An amount to adjust the pH |
| Deionized water | balance |

The above-described shampoo (pH 3.9) can provide hair with good smoothness, moist feeling and suppleness after use.

Example 8

Conditioning Shampoo

| | (wt. %) |
|---|---|
| Sodium polyoxyethylene (2) lauryl ether sulfate | 8.0 |
| Sodium lauryl sulfate | 5.0 |
| Cationized guar gum | 0.5 |
| Amphipathic amide lipid E | 2.0 |
| Glycolic acid | 1.0 |
| Trisodium citrate | 1.0 |
| Laurylamidopropyl betaine | 3.0 |
| 2-Ethylhexyl monoglyceryl ether | 0.7 |
| Myristyl alcohol | 1.0 |
| Ethylene glycol distearate | 3.0 |
| Propylene glycol (Mw = 400) | 0.5 |
| Glycerin | 1.0 |
| Sodium hydroxide | An amount to adjust the pH |
| Deionized water | balance |

The above-described shampoo (pH 3.5) can provide hair with good smoothness, moist feeling and suppleness after use.

Example 9

Conditioning Shampoo

| | (wt. %) |
|---|---|
| Sodium polyoxyethylene (2) lauryl ether sulfate | 8.0 |
| Cationized guar gum | 0.3 |
| Amphipathic amide lipid C | 0.05 |
| Amphipathic amide lipid D | 0.1 |
| Malic acid | 0.5 |
| Glutamic acid | 1.0 |
| Sodium chloride | 1.0 |
| Laurylamidopropyl betaine | 3.0 |
| Myristyl alcohol | 1.0 |
| Cetanol | 0.5 |
| Behenyltrimonium chloride | 0.5 |
| Ethylene glycol distearate | 2.0 |
| Benzyloxyethanol | 0.5 |
| Sodium hydroxide | An amount to adjust the pH |
| Deionized water | balance |

The above-described shampoo (pH 3.9) can provide hair with good smoothness, moist feeling and suppleness after use.

What is claimed is:

1. A hair cleansing composition comprising the following components (A) to (C):
   (A): 0.2 to 3 wt. % of an amphipathic amide lipid selected from the group consisting of

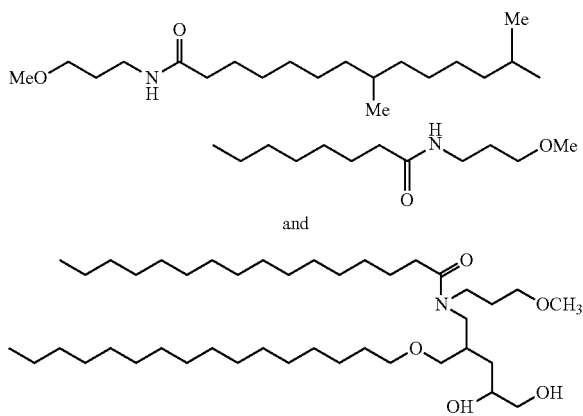

and (B): 10 to 22 wt. % of an anionic surfactant mixture wherein said anionic surfactants are sodium polyoxyethylene (2) lauryl ether sulfate and sodium lauryl sulfate, and
   (C): 0.5 to 2 wt. % of at least one organic acid selected from the group consisting of lactic acid, malic acid, or a salt thereof, wherein the composition has a pH of from 3 to 4 at 25° C. when diluted with water to 20 times the weight of the composition
   further comprising:
   0.1 to 5 wt. % of a cationic polymer selected from the group consisting of cationized hydroxyethyl cellulose and cationized guar gum, and mixtures thereof and
   0.1 to 5 wt. % of cocoylmonoethanolamide.

2. A hair cleansing composition comprising the following components (A) to (C):
   (A): 0.2 to 3 wt. % of an amphipathic amide lipid selected from the group consisting of

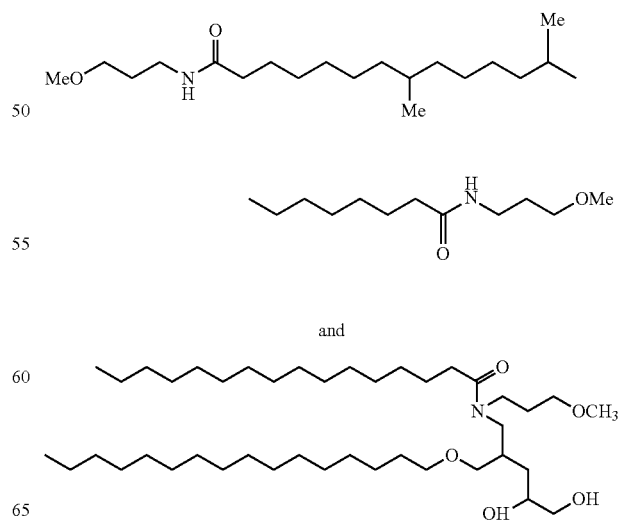

and (B): 10 to 22 wt. % of an anionic surfactant f mixture wherein said anionic surfactants are sodium polyoxyethylene (2) lauryl ether sulfate and sodium lauryl sulfate, and (C): 0.5 to 2 wt. % of at least one organic acid selected from the group consisting of lactic acid, malic acid, wherein the composition has a pH of from 3 to 4.5 at 25° C. when diluted with water to 20 times the weight of the composition further comprising:

0.1 to 5 wt. % of a cationic polymer selected from the group consisting of cationized hydroxyethyl cellulose and cationized guar gum, and mixtures thereof and 0.1 to 5 wt. % of cocoylmonoethanolamide.

* * * * *